United States Patent [19]

Sasayama et al.

[11] Patent Number: 5,945,582
[45] Date of Patent: Aug. 31, 1999

[54] INBRED BROCCOLI LINE BC-403

[75] Inventors: Junichi Sasayama; Shigetoshi Kobayashi, both of Tsu, Japan

[73] Assignee: Sakata Seed America, Inc., Morgan Hill, Calif.

[21] Appl. No.: 08/922,445

[22] Filed: Sep. 3, 1997

[51] Int. Cl.[6] .............................. A01H 5/10; A01H 5/00; A01H 1/04; C12N 5/04
[52] U.S. Cl. ......................... 800/306; 800/295; 800/260; 800/271; 800/273; 800/274; 435/430
[58] Field of Search .................................. 800/200, 205, 800/DIG. 15, 306, 260, 271, 273, 274, 295; 47/DIG. 1; 435/430

[56] References Cited

PUBLICATIONS

Hanson et al. Regeneration of plants from protoplasts of rapid cycling Brassica oleracea L. Plant Cell Reports. 13:335–339, 1994.

*Primary Examiner*—Lynette F. Smith
*Assistant Examiner*—Melissa L. Kimball
*Attorney, Agent, or Firm*—Rothwell, Figg, Ernst & Kurz

[57] ABSTRACT

Inbred broccoli line, designated BC-403 is disclosed. The invention relates to the seeds of inbred broccoli line BC-403, to the plants of inbred broccoli line BC-403, and to methods for producing a broccoli plant produced by crossing the inbred line BC-403 with itself or another broccoli line. The invention further relates to hybrid broccoli seeds and plants produced by crossing the inbred line BC-403 with another broccoli line.

13 Claims, No Drawings

5,945,582

INBRED BROCCOLI LINE BC-403

BACKGROUND OF THE INVENTION

This invention relates to a new and distinctive broccoli inbred line, designated BC-403. There are numerous steps involved in the development of any new and novel desirable germplasm with superior combining ability. Plant breeding begins with the analysis and definition of problems and weaknesses of the current germplasm, the establishment of program goals, and definition of specific breeding objectives. The next step is selection of germplasm that posses the traits to meet the program goals and the best breeding method to reach those goals. The objective is to combine in a single variety or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the cultivar (variety) used commercially (e.g. $F_1$ hybrid, pureline). The complexity of inheritance influences choice of breeding method. A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, observation in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines by selfing followed by selection of desired phenotypes sometimes utilizing anther, microspore and ovule culture to speed up and improve selection efficiency.

The goal of plant breeding is to develop new, unique, and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Description of breeding methods that are commonly used for different traits and crops can be found in one of several reference books. (e.g. Allard, 1960; Simmonds, 1979; Sneep et al., 1979; Fehr, 1987).

Proper testing and evaluation should detect any major faults and establish the level of superiority or improvement over current cultivars. In addition to showing superior performance, there must be a demand for a now cultivar that is compatible with industry standards or which creates a new market. For seed-propagated cultivars, it must be feasible to maintain the inbred lines and produce seed easily and economically.

Broccoli is a new crop in North, South and Central America, Europe and Asia. The introduction of hybrid cultivars in the 1960's provided a magnitude increase in yield, holding ability, expanded growing seasons and large scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea,* Italica group) belongs to the mustard family. All *Brassica oleracea* will cross pollinate. Pollination is effected by insect vectors, most common of which is the honey bee. Broccoli, like most other Brassica, have a genetic characteristic of self incompatibility which encourages cross pollination resulting in higher levels of variability. Variability in populations is desired for wide adaptation and survival. Broccoli breeding populations can be inbred or backcrossed for 8 to 9 generations and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross pollinated species. This breeding system in nature has been utilized by man in $F_1$ hybrid breeding, especially in Brassica vegetables (Tsunoda et al., chapter 13).

Cytoplasmic male sterility (CMS) is another method used in Brassica vegetables species to produce $F_1$ hybrids. This method of producing hybrids in Brassica is a more recent development compared to self-incompatibility. A genetic mutation contained in the cytoplasm (mitochondria) is responsible for the lack of production of pollen. In Brassica, the cytoplasm has commonly been identified in and transferred from "Ogura"-type radish (Ogura, 1968). The major advantage of CMS over self-incompatibility is that under normal conditions, no pollen is produced in the female parent. This results in the production of 100% hybrid seed. Under certain stressful growth conditions, however, it may be possible to produce small amounts of fertile pollen in CMS plants. Brassica inbreds containing CMS are maintained by continued hybridization to their normal (fertile) counterpart inbred, commonly referred to as a "B" line. The plants associated with the Brassica group have been familiar to mankind since ancient times, and always of great agricultural importance. Brassica is a major food species worldwide. Brassica species have a general adaptation for cool climate growing conditions. Therefore, adaptation has occurred for summer growing conditions with cool to moderate climates and for winter growing conditions in warmer or tropical locations.

SUMMARY OF THE INVENTION

The invention comprises a novel inbred broccoli line, designated BC-403. This invention thus relates to the seeds of inbred broccoli line BC-403, to the plants of inbred broccoli line BC-403, to methods used for controlling pollination when making hybrid seed with BC-403, and to methods for producing a broccoli plant by crossing the inbred broccoli line BC-403 with itself or another broccoli line. This invention further relates to hybrid broccoli seeds and plants produced by crossing the inbred line BC-403 with another broccoli line

DETAILED DESCRIPTION OF THE NEW PLANT

Definitions

In the description and tables which follow, a number of terms are used. In order to provide a clear and consistent understanding of the specification and claims, including the scope to be given such terms, the following definitions are provided.

Plant Height: Plant height is measured in centimeters from the soil line to the top of the leaves.

Head Height: Head height is measured in centimeters from the soil line to the top of the head.

Leaf Width: Leaf width is measured in centimeters at the midpoint of the plant including the petiole.

Leaf Length: Leaf length is measured in centimeters from the midpoint of the plant including the petiole.

Head Diameter: Head Diameter is measured at the widest diameter of the head (from overhead) in centimeters.

Head Depth: Head Depth is measured in centimeters from the top of the head to the lowermost florets.

Stem Diameter: Stem diameter is measured in centimeters and is taken at a point just below the head.

Maturity: Plants are considered mature when the head and stem have developed to the fresh market maturity stage.

Yield: The yield is the weight in grams for a harvested broccoli head or floret cluster.

Overall Rating Score: This Overall Rating Score is rated on a scale of 1 to 5. A score of 5 indicated an excellent overall rating. A score of 3.0 indicates average, and a score of 1 indicates poor.

Color: Color means the color of the head at maturity.

Field Holding Ability: Field Holding Ability means the ability of a plant to maintain good head quality (i.e. small, firm, green heads) after the optimal harvest date.

Disease and Insect Ratings: Disease and Insects are rated on a scale of 1 to 5. A score of 5 indicates severe damage. A score of 3.0 indicates moderate damage, and a score of 1 indicates no damage.

Inbred broccoli BC-403 is a heading broccoli (*Brassica oleracea* Italica group) with superior characteristics, and provides an excellent parental line in crosses for producing first generation ($F_1$) hybrid broccoli.

Inbred line BC-403 was developed, beginning in 1974, by hybridization between U.S.A. variety "No. 5" (source unknown) and an Asian domestic variety "No. 183" (source unknown) and grown at the Kimitsu Research Station, Japan. Pedigree selection for small bead size and good seed set then followed for 3 years. Subsequently, in 1978, one plant was crossed with another U.S.A. variety, "No. 115" (source unknown). Pedigree selection then continued for good seed set, good plant habit, and vigor until 1985, when one fixed line, GIX, was selected. Cytoplasmic male sterility was transferred to inbred GIX from an Ogura-derived CMS source developed by Sakata Seed Corporation. The inbred line UL was crossed to the CMS source and the resulting progeny were backcrossed to GIX seven times to recover the GIX background.

The inbred has shown uniformity and stability for all traits, as described in the following variety description information. The line has been increased and maintained by pollination with fertile inbred line GIX with continued observation for uniformity.

The inbred broccoli line BC-403 has the following morphologic and other characteristics. The data were collected in the 1996 fall/winter season at Salinas, Calif.

VARIETY DESCRIPTION INFORMATION

MATURITY: Very late, approximately 106 days from sowing

PLANT CHARACTERISTICS:

Habit: Compact
Plant Heights: 52 cm
Leaves: 37 cm average length at mid-point of the plant (including petiole), 9 cm width at mid-point of the plant, 4:1 length to width ratio
Leaf Margins: Very wavy
Veins: Thin
Petiole Attachment: Petiolate
Anthocyanin Coloration: No coloration
Inflorescence: Small to medium flower bud size, yellow flowers, many side sprouts after head harvest, 12 cm center head diameter, 8 cm center head depth, 3 cm diameter of stem base of head, good compactness of center head, dark blue-green center head color.

This invention is also directed to methods for producing a broccoli by crossing a first parent broccoli plant with a second parent broccoli plant, wherein the first or second broccoli plant is the inbred broccoli from the line BC-403. Further, both first and second parent broccoli plants may be from the inbred line BC-403. Therefore, any methods using the inbred broccoli line BC-403 are part of this invention; selfing, backcrosses, hybrid breeding, and crosses to populations. Any plants produced using inbred broccoli line BC-403 as a parent are within the scope of this invention. Advantageously, the inbred broccoli line is used in crosses with other broccoli varieties to produce first generation ($F_1$) broccoli hybrid seed and plants with superior characteristics.

As used herein, the term "plant" includes plant cells, plant protoplasts, plant cells of tissue culture from which broccoli plants can be regenerated, plant calli, plant clumps, and plant cells that are intact in plants or parts of plants, such as pollen, flowers, seeds, stalks, stumps, leaves and the like. Thus, another aspect of this invention is to provide for cells which upon growth and differentiation produce the inbred broccoli BC-403.

TABLE

In Table 1 that follows, the traits and characteristics of inbred broccoli line BC-403 are given in hybrid combination. The data collected on hybrids containing inbred broccoli line BC-403 as one parent is presented. The table presents overall rating scores and additional characteristics. BC-403 was tested in several hybrid combinations at different locations over a number of years. Information about these hybrids, as compared to several check hybrids, is presented. Column 2 shows the overall rating which ranges from 1–5, with 5 being the best overall rating. Column 3 lists various characteristics of the specific hybrid.

TABLE 1

Combining ability of inbred line BC-403. Plants were grown in Salinas, CA and evaluated in November of 1996.

| HYBRID | OVERALL RATING | ADDITIONAL CHARACTERISTICS |
| --- | --- | --- |
| Line A × BC-403 | 3.3 | Med-sm. bead, good dome shape, some heat damage |
| Line A × B | 2.5 | Much heat damage, flat, low head position, not vigorous |
| Line A × C | 2.5 | Leafy head with uneven bead, semi-flat, downy mildew susceptible |
| Line A × D | 3.0 | Uneven bead, semidome, slightly loose, downy mildew susceptible |
| Line A × E | 3.1 | Small bead, some heat damage, slightly loose and lumpy, dwarf |
| Line F × BC-403 | 2.8 | Much heat damage, small bead, dome, tight, slightly lumpy |
| Line F × G | 1.5 | Small bead, lower vigor, very bad heat damage, flat head |
| Line F × H | 2.5 | Small bead, much heat damage, tight, semidome, slightly lumpy |
| Line F × E | 2.5 | Much uneven bead and heat damage, dome, round shape |
| Line F × I | 3.2 | Small bead, pale green, slightly lumpy, tight, some uneven bead |
| Line J × BC-403 | 3.0 | Some head leafiness, small bead, some cateye, semiflat |
| Line J × K | 3.3 | Small bead, lumpy, some heat damage and brown bead |
| Line J × L | 3.0 | Medium bead, semiflat, slightly loose |
| Line J × M | 3.1 | Medium bead, loose, semiflat, pale green, high head position |

In Table 2 that follows, the traits and characteristics of inbred broccoli line BC-403 are given. The table represents overall mean scores for each characteristic. Column 1 show the plant height, column 2 shows the head height. Columns 3 and 4 are leaf width and length. Columns 5 and 6 indicate the head diameter and depth and column 7 indicates the stem diameter. All figures are given in centimeters

TABLE 2

1997 mean averages of GC-403

| Plant Ht. | Head Ht. | Leaf Width | Leaf Length | Head Diameter | Head Depth | Stem Diameter |
| --- | --- | --- | --- | --- | --- | --- |
| 59.6 | 33.4 | 15.7 | 50.1 | 10.2 | 5.8 | 3.3 |

DEPOSIT INFORMATION

A deposit of the Sakata Seed America, Inc. Inbred Broccoli Line BC-403 disclosed above and recited in the appended claims has been made with the American Type Culture Collection (ATCC), 10801 University Boulevard, Manassas, Va. 20110 The date of deposit was Apr. 13, 1999. The deposit of 2,500 seeds were taken from the same deposit maintained by Sakata Seed America, Inc. since prior to the filing date of this application. All restrictions upon the deposit have been removed, and the deposit is intended to meet all of the requirements of 37 C.F.R §1.801–1.809. The ATCC accession number is ATCC 203920. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred broccoli seed designated BC-403 having ATCC accession No. 203920.

2. A broccoli plant produced by growing the seed of claim 1.

3. Pollen of the plant of claim 2.

4. An ovule of the plant of claim 2.

5. An inbred broccoli plant having all the physiological and morphological characteristics of the broccoli plant of claim 2.

6. A broccoli plant regenerated from a tissue culture of tissue obtained from the broccoli plant of claim 2, said regenerated broccoli plant capable of expressing all the physiological and morphological characteristics of said broccoli plant of claim 2.

7. A method of producing first generation ($F_1$) hybrid broccoli seed comprising crossing an inbred parent of broccoli and a second inbred broccoli plant and harvesting the resultant first generation ($F_1$) hybrid broccoli seed, wherein said first or second parent broccoli plant is the broccoli plant of claim 2.

8. The method of claim 7 wherein the said broccoli plant is the female parent.

9. The method of claim 7 wherein said broccoli plant is the male parent.

10. A first generation ($F_1$) hybrid broccoli plant produced by growing said hybrid broccoli seed of claim 7.

11. The method of claim 7 wherein said broccoli hybrid seed is produced using self-incompatibility.

12. The method of claim 7 wherein the said hybrid broccoli seed is produced using male sterility.

13. Seed produced by growing the hybrid broccoli plant of claim 10.

* * * * *